United States Patent
Venturino et al.

(10) Patent No.: US 6,702,917 B1
(45) Date of Patent: Mar. 9, 2004

(54) CROSS-MACHINE-DIRECTION NESTED ABSORBENT PADS WITH MINIMAL WASTE GEOMETRIES

(75) Inventors: Michael B. Venturino, Appleton, WI (US); Leon R. Flesburg, Neenah, WI (US); Mark C. Jacobs, Appleton, WI (US); David W. Heyn, Neenah, WI (US); Jennifer L. Dopke, East Troy, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/233,331

(22) Filed: Aug. 30, 2002

(51) Int. Cl.[7] .............................................. B32B 31/18
(52) U.S. Cl. ....................... 156/252; 428/219; 428/220; 428/192; 428/98; 83/284; 83/436.6; 83/803; 118/109; 118/264; 156/250
(58) Field of Search .................................. 83/284, 436.6, 83/803; 118/109, 264; 428/98, 192, 219, 220; 156/252, 250

(56) References Cited

U.S. PATENT DOCUMENTS

| | | |
|---|---|---|
| 4,862,574 A | 9/1989 | Seidy |
| 5,580,411 A | 12/1996 | Nease et al. |
| 5,587,437 A | 12/1996 | Adachi et al. |
| 5,695,846 A * | 12/1997 | Lange et al. ............. 428/98 |

FOREIGN PATENT DOCUMENTS

| | | |
|---|---|---|
| EP | 0280998 A1 | 9/1988 |
| EP | 0539032 B1 | 12/1996 |
| EP | 0670153 B1 | 12/1998 |
| EP | 1062928 A1 | 12/2000 |
| WO | 0232357 A2 | 4/2002 |

OTHER PUBLICATIONS

U.S. application Ser. No. 09/975,103, filed Oct. 10, 2001.
EPO Search Report, Sep. 12, 2003.

* cited by examiner

*Primary Examiner*—David W. Wu
*Assistant Examiner*—William Cheung
(74) *Attorney, Agent, or Firm*—Dority & Manning

(57) ABSTRACT

A method is provided for making absorbent pads that may have a longitudinally asymmetric shape. The pads may be used in various consumer absorbent articles. The method includes delivering a supply of an absorbent web material in a machine-direction and cutting the absorbent web material in a cross-direction to form a repeating nested pattern of generally identically shaped and oppositely oriented absorbent pads, the pads being disposed longitudinally in the cross-direction of the absorbent web. The pads are longitudinally asymmetric and nested such that the crotch portion of one pad is oriented towards the back portions of immediately adjacent pads, and adjacent nested pads share defining cut lines such that there is no wastage of absorbent web material between the nested pads.

39 Claims, 5 Drawing Sheets

CROSS-MACHINE-DIRECTION NESTED ABSORBENT PADS WITH MINIMAL WASTE GEOMETRIES

TECHNICAL FIELD OF THE INVENTION

The present invention relates generally to the field of forming shaped absorbent pad structures from an absorbent web, the pads being suitable for use in disposable absorbent articles such as diapers, child's training pants, feminine care articles, incontinence articles, swim pants, and the like.

BACKGROUND

Many types of disposable consumer products such as diapers, training pants, feminine care articles, incontinence articles, and the like, utilize an absorbent pad structure for absorbing and wicking away bodily fluids. The absorbent pads are conventionally formed from an absorbent web, typically a non-woven fibrous web material formed by known techniques. For example, the absorbent web may be formed by employing conventional air forming techniques wherein fibers and typically a superabsorbent material are mixed and entrained in an air stream and then directed onto a forming surface to form the web. The absorbent web may then be directed for further processing and assembly with other components to produce a final absorbent product.

With another conventional technique, preformed absorbent web sheets or layers are delivered into a manufacturing line from a preformed supply, such as a supply roll. The sheets or layers have been separated into adjacent strips having various configurations of repeat pattern "nested" shapes wherein the shape of one strip is substantially nested with the shape of at least one immediately adjacent strip.

Absorbent web material formed on a remote base machine and supplied to the manufacturing line from a roll or other supply form generally has a significant cost disadvantage as compared to air laid webs formed on a converting machine. With the air laid web, the trim waste can be immediately recycled by returning the waste to the upstream fiberizing equipment. On the other hand, with the roll material, the geographical separation of the base machine makes recycling of the trim waste impractical and often cost prohibitive. In this regard, the nesting feature mentioned above has been desirable to reduce the amount of waste that is generated from the supply (roll) of absorbent web It has been recognized that particular nested strip shapes can be more readily adapted to high-speed manufacturing processes. The more easily processed strip-shapes have a repeat pattern that is substantially symmetrical with respect to their longitudinal dimension, the shapes being arranged longitudinally in the machine-direction of the web. With such longitudinally-symmetric nested patterns, a single cycle of the repeat pattern provides an individual web segment wherein the shape of a first lengthwise half portion of the segment substantially matches the shape of the longitudinally opposed other half portion. However, such longitudinally symmetric pads have been shown, in certain application, to be less desirable from an end product fit, comfort, and performance aspects.

As a result, it has been desirable to construct absorbent pads from web segments that are longitudinally-asymmetric. With such a construction, the resulting pads may provide improved product fit, comfort, and performance. However, the dividing of an absorbent web into strips having a nested pattern shape of longitudinally asymmetric segments generates a significant amount of trim waste, particularly along the machine-direction sides of the absorbent web.

Examples of suggestions in the art to reduce trim waste may be found, for example, in U.S. Pat. Nos. 5,587,437; 5,695,846; 5,580,411; 4,862,574; EP 0 539 032; and EP 0 670 153.

The present invention provides a method for producing longitudinally asymmetric nested pad structures in a continuous absorbent web wherein there is virtually zero waste of the web material.

SUMMARY OF THE INVENTION

Objects and advantages of the invention will be set forth in part in the following description, or may be obvious from the description, or may be learned through practice of the invention.

The present invention provides an improved method for making absorbent pads having a longitudinally asymmetric shape. Such pads may be used in various applications of disposable consumer absorbent articles, such as diapers, child's training pants, feminine care articles, incontinence articles, swim pants, and the like. The pads are longitudinally asymmetric in that the back portion has a different shape or configuration as compared to the crotch or front portion of the pad. As mentioned, longitudinally asymmetric pads of this type have proven to be superior with respect to product fit, comfort, and performance as compared to longitudinally symmetric pads. The present method provides a technique for mass producing such pads from a continuous strip of absorbent web material in a manner so that there is virtually zero waste of the web material.

In accordance with one embodiment of the present method, the absorbent web material is delivered in the form of a continuous strip or series of adjacent strips, for example from a supply roll, in a machine-direction flow. In other words, the parallel sides of the strip of material lie in the machine-direction. The absorbent web material is cut in a cross-direction to form a repeating nested pattern of cross-directional and generally identically shaped pads. The pads are nested in that any two adjacent pads forming a nested pair are oriented in longitudinally opposite directions in the cross-direction of the absorbent web. In other words, the longitudinal centerline of the pads lies generally perpendicular to the machine-direction of the web material.

The pads are defined by cross-directional cuts such that the crotch portion of one pad is oriented towards the back portions of immediately adjacent pads. Adjacent nested pads share common defining cut lines such that there is no wastage of absorbent material between the nested pads. Each pad is longitudinally asymmetric with respect to the crotch and back portions. For example, in one particular embodiment, the back portion of the pads includes ears that define the widest width of the pad, with a smaller width crotch section extending longitudinally from the ears and back portion.

In one particular embodiment, the individual absorbent pads are defined across the strip of absorbent web material such that each pad has a longitudinal length that is less than the cross-directional width of the web material. In this embodiment, however, a nested pair of the absorbent pads has a combined nested longitudinal length that is equal to the cross-directional width of the web material. For example, according to this particular embodiment, the absorbent pads may be generally T-shaped with a back ear portion having a width measured in the machine-direction that is about twice that of the center crotch portion. The pads are symmetrical about a longitudinal centerline axis therethrough. In other words, the pads can be symmetrically folded lengthwise. In this particular embodiment, the back ear portion may have a height defined by a cross-directional cut line that is shared by the next commonly oriented pad in the repeating pattern. Thus, all of the pads having the crotch portions oriented in one direction would have adjacent ears defined by a common cross-directional cut line. The oppositely oriented or nested pads have crotch portions nested against the ears of their respective adjacent pads. With this particular arrangement, the cut line defining the ears of adjacent commonly oriented pads corresponds to the longitudinal centerline of the pad nested therebetween.

In another embodiment of a generally T-shaped absorbent pad, the crotch portion has a first longitudinally extending section having a first width, this section diverging along lines into a longitudinally extending second section having a second greater width. With this embodiment, the pads are still symmetrical about their longitudinal centerline axis. The diverging lines between the first width section and the second width section have a center point through which the machine-direction centerline axis of the strip of web material passes. This line may be straight or sinusoidal. The sides of the crotch section along the first width and second greater width sections may be generally parallel.

In still further embodiments, the absorbent pads are defined with cross-directional cuts such that each pad has a longitudinal length equal to the cross-directional width of the strip of absorbent web material. In this embodiment, a single cross-directional cut line defines a common longitudinal side of adjacent nested pads. These pads may have a back ear portion with a center crotch portion extending longitudinally therefrom. An angle of divergence is defined at a cut line between the crotch portion and the ear portion that corresponds to the same angle for the immediately adjacent and oppositely oriented pad. This cut line may be generally straight or sinusoidal, and has a center point through which the machine-direction centerline axis of the strip of web material passes.

The method will be explained in greater detail below by reference to particular embodiments thereof.

DETAILED DESCRIPTION

Figure 1:
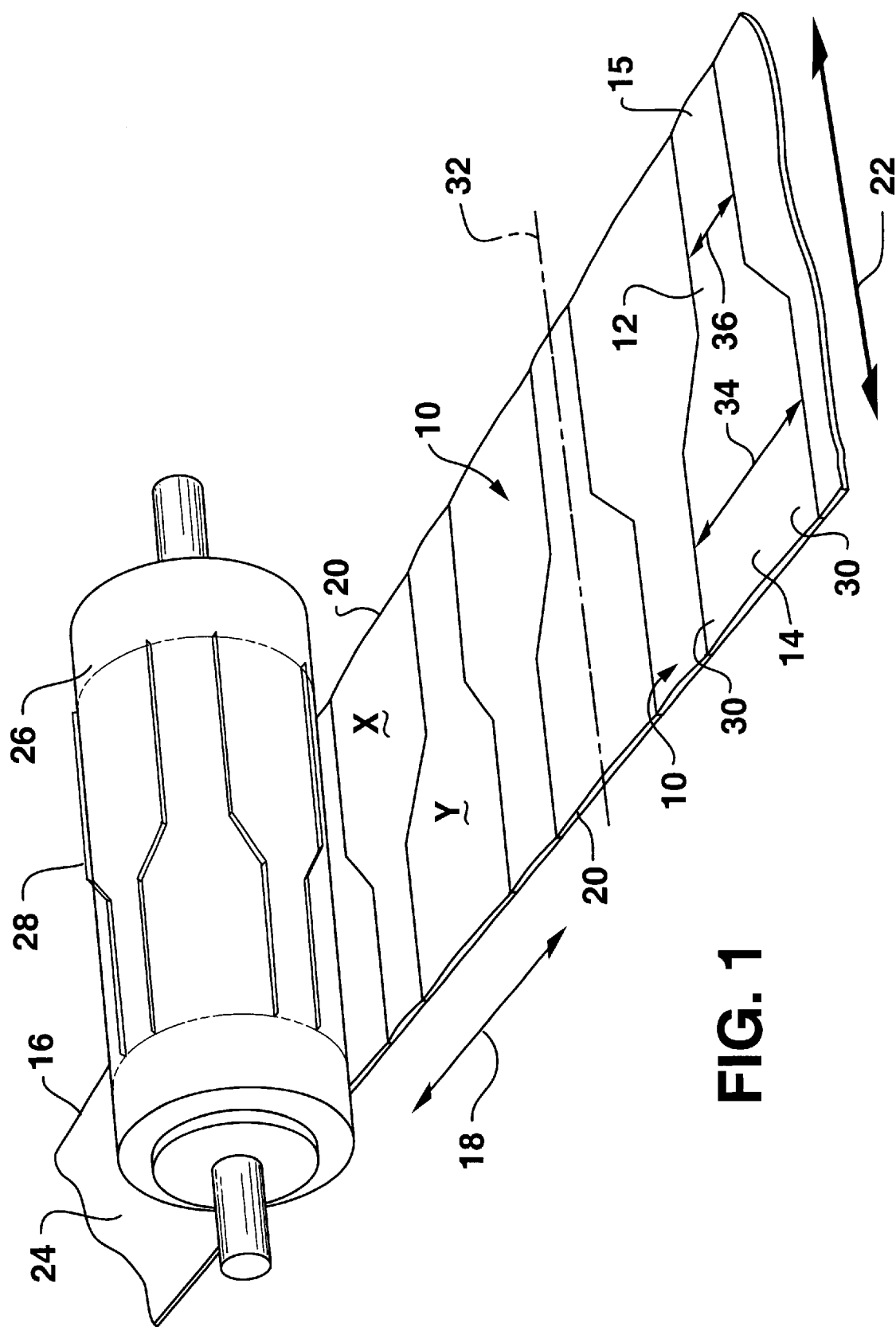
FIG. 1 shows a perspective view of a strip of absorbent web material being cut into a repeating pattern of nested cross-directionally disposed absorbent pads.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

The present method is particularly suited for the manufacture of pad structures from a web of absorbent material, the pads intended for use in various disposable consumer absorbent products. Such products include, but are not limited to, diapers, child's training pants, feminine care articles, incontinence articles, swim pants, and the like. The invention is not limited to any particular type or composition of absorbent web material, and may be practiced with any suitable absorbent web material known to those skilled in the art. The absorbent web material may include any structure and combination of components which are generally compressible, conformable, non-irritating to a wearer's skin, and capable of absorbing and retaining liquids and certain body wastes.

For example, the absorbent web material may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One suitable type of fluff is identified with the trade designation CR 1654, available from U.S. Alliance Corp. of Coosa Pines, Ala., and is a bleached, highly absorbent sulfact wood pulp containing primarily soft wood fibers. As a general rule, the superabsorbent material is present in the absorbent web in an amount of from about 5 to about 90 weight percent based on total weight of the web. The web may have a density, for example, within the range of about 0.10 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a suberabsorbent material is capable of absorbing at least about 15 times its weight in liquid, and desirably is capable of absorbing more than about 25 times its weight in liquid. Suitable superabsorbent materials are readily available from various suppliers. For example, Favor SXM 880 superabsorbent is available from Stockhausen, Inc., of Greensboro, N.C., USA; and Drytech 2035 is available from Dow Chemical Company, of Midland Mich., USA.

Subsequent to or after being cut from the nested pattern as described herein, the individual absorbent pads may be partially or wholly wrapped or encompassed by a suitable tissue wrap that aids in maintaining the integrity and shape of the pad.

The absorbent materials may be formed into a web structure by employing various conventional methods and techniques. For example, the absorbent web may be formed with a dry-forming technique, an airlaying technique, a wet-forming technique, a foam-forming technique, or the like, as well as combinations thereof. Methods and apparatus for carrying out such techniques are well known in the art.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

In a particular aspect of the invention, the absorbent web material can be provided with an absorbent capacity of at least about 8 g/g employing 0.9 wt % saline (8 grams of 0.9 wt % saline per gram of absorbent web). The absorbent capacity of the absorbent web can alternatively be at least about 9 g/g, and can optionally be at least about 10 g/g to provide improved benefits. Additionally, the absorbent capacity may be up to about 50 g/g, or more, to provide desired performance.

In another aspect, the web of absorbent material can be provided with a tensile strength value of at least about 1 N/cm (Newtons per cm of "width" of the material, where the "width" direction is perpendicular to the applied force). The tensile strength of the absorbent web can alternatively be at least about 1.5 N/cm, and can optionally be at least about 2 N/cm to provide improved benefits. In another aspect, the web of absorbent material can be provided with a tensile strength value of up to a maximum of about 100 N/cm, or more. The tensile strength of the absorbent web can alternatively be up to about 10 N/cm, and can optionally be up to about 20 N/cm to provide improved benefits.

The selected tensile strength should provide adequate processibility of the web throughout the manufacturing process, and can help to produce articles that exhibit desired combinations of softness and flexibility.

The absorbent material web is also selected so that the individual absorbent pad structures possess a particular individual total absorbency depending on the intended article of use. For example, for infant care products (e.g., diapers), the total absorbency can be within the range of about 300–900 grams of 0.9 wt % saline, and can typically be about 500 g of saline. For adult care products, the total absorbency can be within the range of about 1000–1600 grams of saline, and can typically be about 1300 g of saline. For feminine care products, the total absorbency can be within the range of about 7–50 grams of saline, and can typically be within the range of about 30–40 g of saline.

Aspects of the present method include delivering a supply of the absorbent web material in a machine-direction flow. The web material is delivered in the form of a continuous ribbon or strip from a supply source, such as a roll. Optionally, the web strip may be supplied directly from an in-line manufacturing operation. The "machine-direction" is the direction along which the strip travels length-wise through a particular processing stage. The web material strip has a "cross-direction" or "width" that is perpendicular to the machine-direction. The material also has a depth-wise "z" direction that is perpendicular to the cross-direction and machine-direction.

Referring to FIG. 1, an absorbent web material 16 is supplied in the form of a ribbon or strip 24. As mentioned, the web material 16 may be supplied from a roll or directly from an in-line manufacturing operation. The strip of web material 24 is conveyed in a machine-direction 18 and has machine-direction sides 20 defined by opposite parallel sides of the strip 24. The strip of web material 24 also has a cross-direction dimension 22 that may be considered as the "width" of the strip 24. FIG. 1 illustrates a single strip of web material 24, however, it should be appreciated that an absorbent web material may be supplied in the form of a plurality of adjacent strips 24. After the absorbent pads 10 have been defined in the strips according to the present invention, the plurality of strips could be separated for subsequent delivery to an absorbent article manufacturing line.

Still referring to FIG. 1, the strip 24 of absorbent web material is cut in the cross-direction 22 to form a repeating nested pattern of cross-directional absorbent pads 10. The pads 10 are oriented so that a longitudinal centerline axis 32 thereof lies in the cross-direction 22 of the strip 24. The pads are nested in that any two adjacent pads form a nested pair and are oriented in longitudinally opposite directions in the cross-direction 22 of the absorbent pad. For example, referring to FIG. 1, absorbent pad X is nested with absorbent pad Y such that a crotch section 12 of pad Y is oriented towards a front portion 14 of pad X.

As described in greater detail below with respect to the remaining figures, the absorbent pads 10 may desirably have a longitudinally asymmetric shape wherein the crotch portion 12 and front portion 14 have different widths. The pads are, however, in particular embodiments symmetrical with respect to the longitudinal axis 32 defined therethrough. In other words, the pad may be folded along the axis 32 into symmetric halves. In alternate embodiments, the pads 10 may be non-symmetrical with respect to the axis 32.

Referring to FIG. 1, the process of cutting the strip 24 of web material with cross-direction cuts in order to define the individual absorbent pads 10 is illustrated as carried out by a conventional and schematically illustrated rotary knife or roll 26 having blades 28 defined thereon in a pattern corresponding to the nested shape of the pads 10. It should be appreciated that any suitable cutter mechanism may be utilized in this regard, including future developed methods and devices. Conventional cutter mechanisms and devices are well known in the art, and can include rotary knives, die cutters, water-cutters, laser cutters, and the like, as well as combinations thereof. The method according to the present invention is not limited by any particular cutting method or apparatus.

Referring again to FIG. 1, it can be seen that the adjacent nested pads 10 share common defining cut lines such that there is a minimum of wastage of absorbent material between the nested pads 10. In the embodiment of FIG. 1, there is minimum or no wastage of material. With conventional nested patterns, there is typically between about 30% to about 35% wastage of material between adjacent pads. The present invention encompasses nested configurations wherein the wastage is minimal, desirably less than about 20%, and more desirably at zero wastage. The ability to mass produce longitudinally asymmetric pads without wastage of the web material is a significant feature. The pads have a crotch section generally designated as 12, a "back" section 15, and a longitudinally opposite "front" portion generally designated as 14. The crotch section 12 and back section 15 may be considered as a common section, particularly if they have the same shape and dimensions as in FIGS. 2 and 3. The front portion 14 is configured for the waist band portion of an absorbent article and includes "ears" 30 that define the widest width dimension of the pad 10. Accordingly, each pad 10 may have a minimum crotch width 36 and a maximum waist band or front section width 34. The ratio of the front section width to the crotch width can be at least about 1.5 to 1. Alternatively, the front section to crotch width ratio may be at least about 2 to 1, and can optionally be about 3 to 1. Additionally, the waist band to crotch width ratio can be up to about 10 to 1 to provide desired levels of fit and performance.

It should also be appreciated that the crotch width 36 can be tailored for particular desired absorbent articles. For example, in an absorbent pad 10 designated for a feminine care article, the crotch width 36 may be within the range of about 2 to 5 centimeters. In a particular feminine care configuration, the crotch width can be about 3.8 centimeters (about 1.5 inches). For an absorbent pad designated for an infant care article, the crotch width can be within the range of about 4 to 12 centimeters. In a particular infant care configuration, the crotch width can be about 10 centimeters (about 4 inches). For an absorbent pad designated for an adult care article, the crotch width can be within a range of about 7 to 20 centimeters. In a particular adult care configuration, the crotch width can be about 15 centimeters (about 6 inches).

Figure 2:
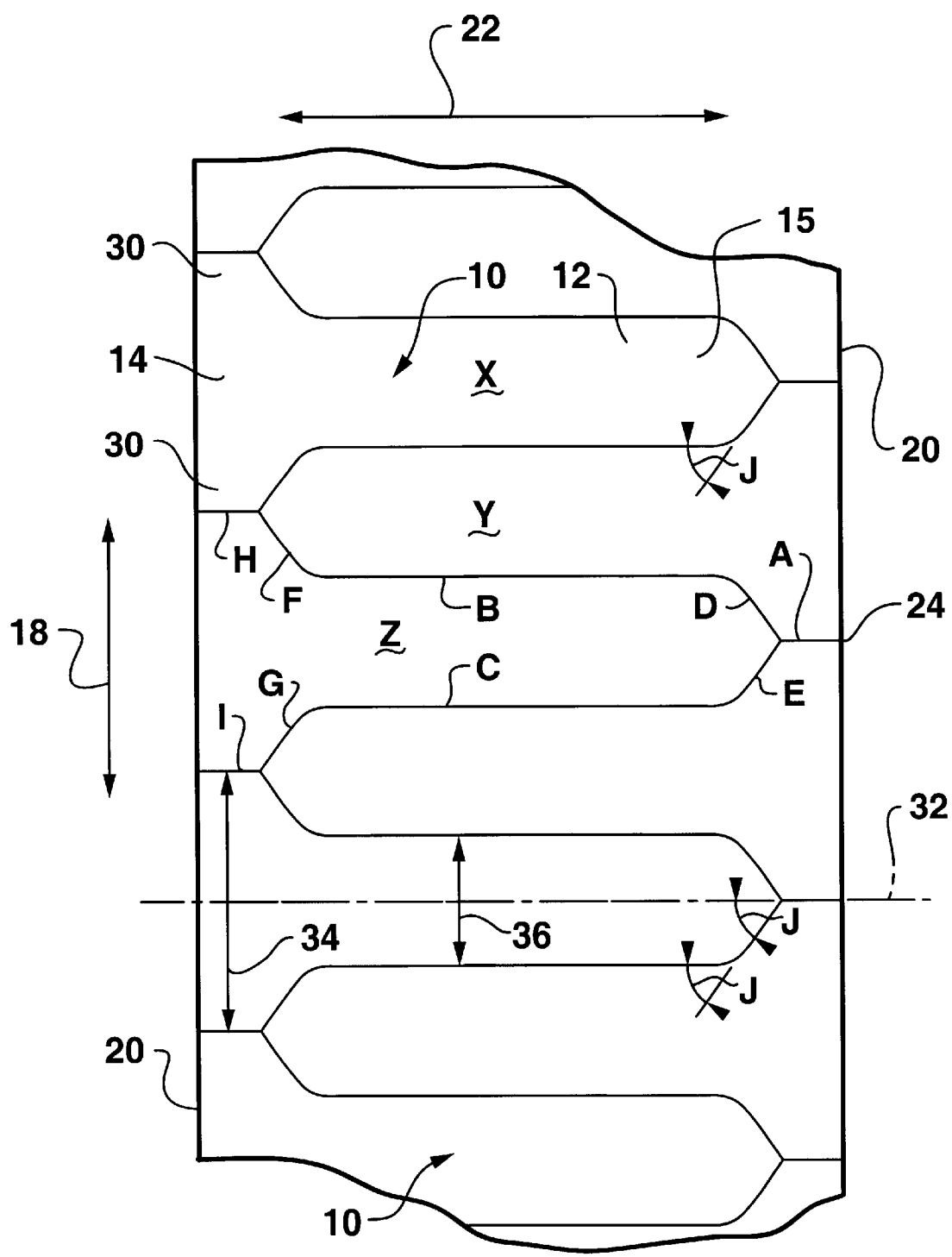
FIG. 2 shows a representative top view of an alternate embodiment of an alternating pattern nested configuration according to the present method.
Figure 3:
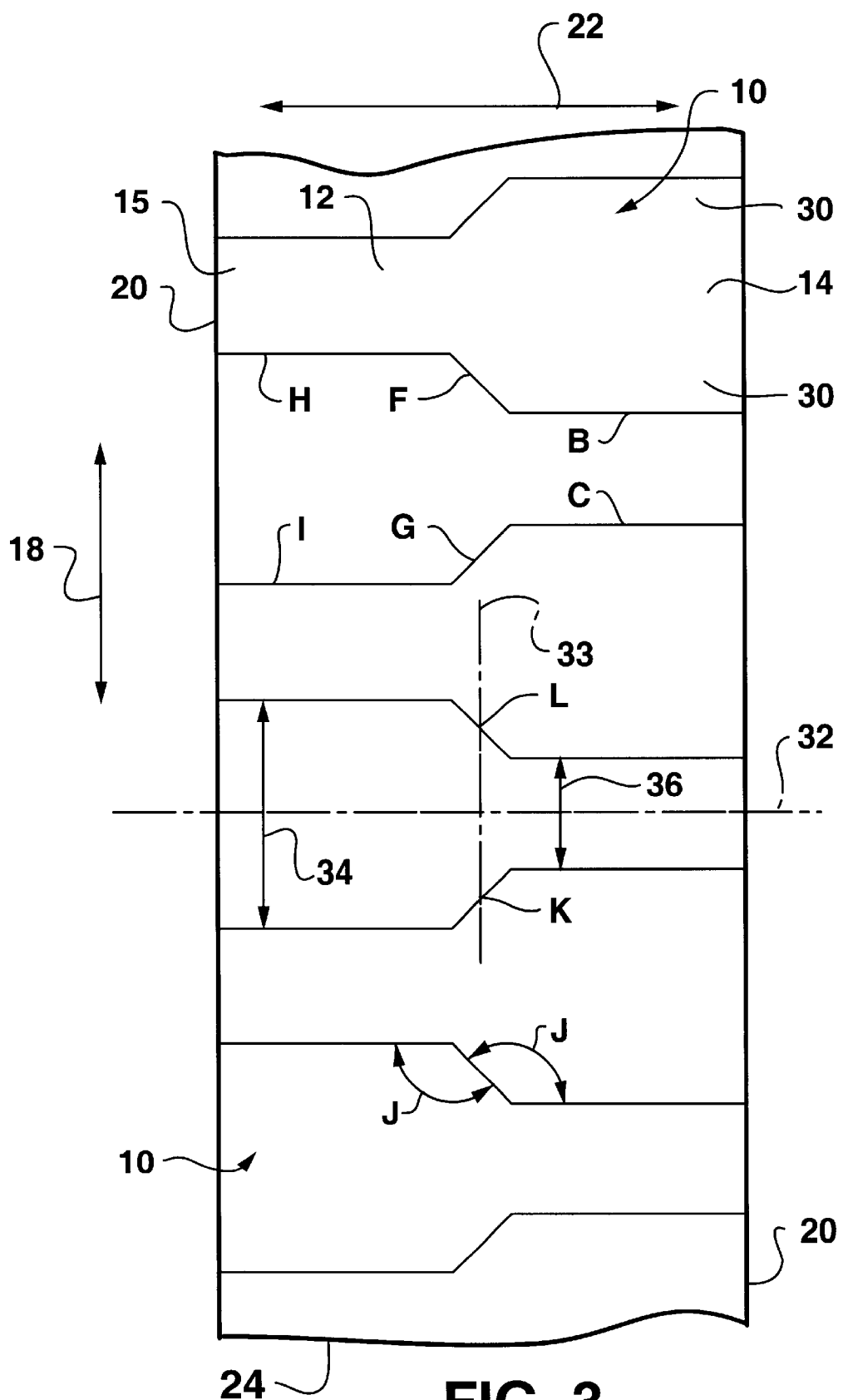
FIG. 3 is a representative top view of the repeating nested pattern configuration illustrated in FIG. 1.
Figure 4:
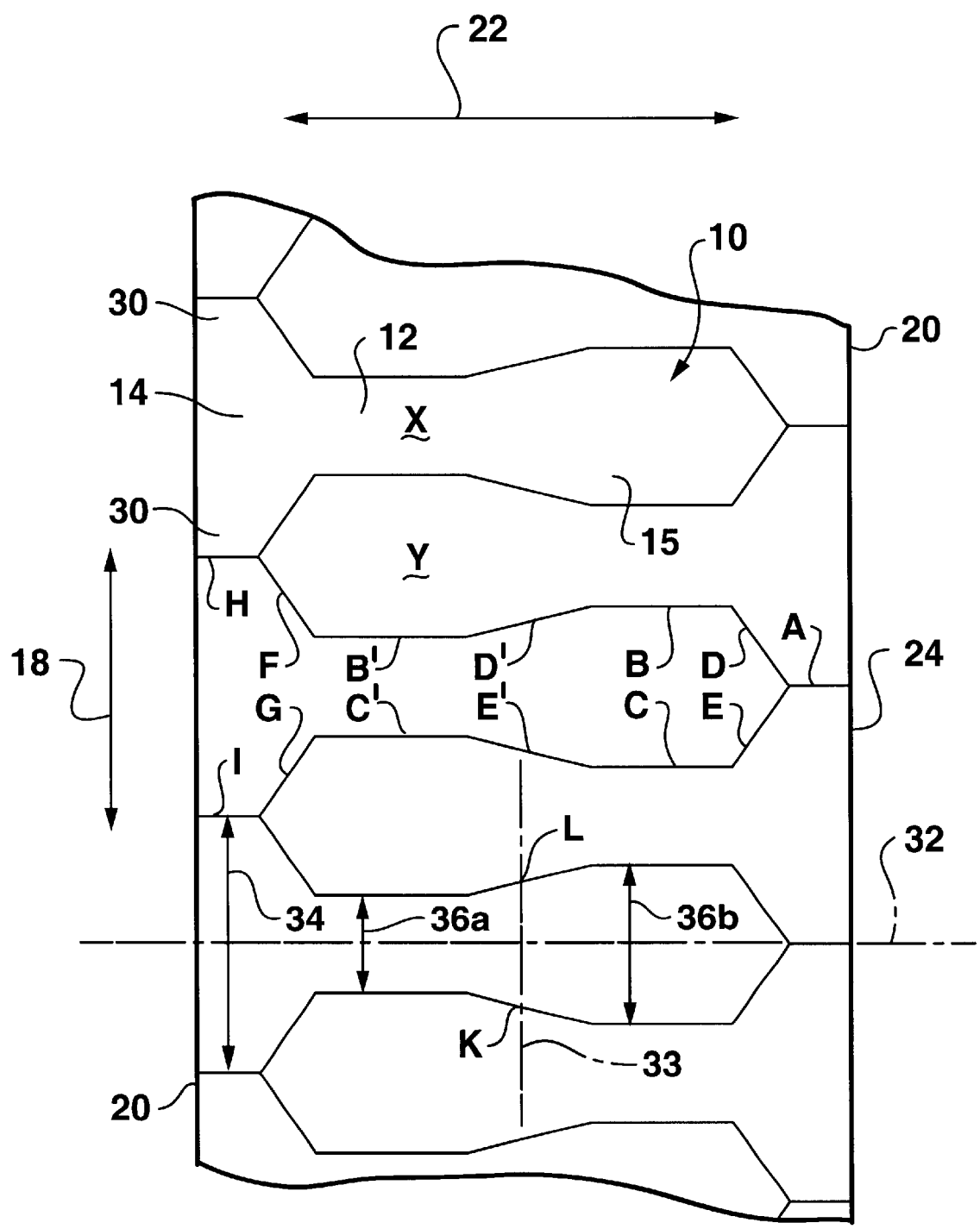
FIG. 4 shows a representative top view of still another embodiment of a repeating nested configuration according to the invention.

It should be appreciated that a vast number of shapes and configurations are possible for defining the cross-directional nested pads 10 in accordance with the invention, particularly for longitudinally asymmetric pads as described herein. The pads 10 will generally have an identical shape and will be symmetrical with respect to the longitudinal axis 32 therethrough. The longitudinal orientation of the pads will alternate, and alternate pads will share common defining cuts or chords so that there is virtually no wastage of absorbent material between adjacent pads. Particular embodiments of pad configurations within the scope of the invention are illustrated in FIGS. 2 through 4. It should be appreciated, however, that such embodiments are for illustrative purposes only, and that the invention is not limited to any particular configuration.

Referring to FIG. 2, a nested configuration of cross-directionally oriented pads 10 is illustrated. In this particular embodiment, the pads 10 have a generally T-shaped configuration with the front section 14 including ears 30. A relatively constant width crotch section 12 extends longitudinally from the front section 14. A longitudinal centerline axis 32 may be defined through the pad 10. The crotch section 12 has a relatively constant width designated by the arrow 36. The front portion 14 with ears 30 defines the widest width dimension 34 of the pad 10. In this particular embodiment, the pad has an overall length that is less than the cross-directional width of the web strip 24. However, a nested pair of the absorbent pads, for example pads X and Y in FIG. 2, have an overall combined longitudinal length that is equal to the cross-directional width of the web strip 24. For example, particularly with generally T-shaped pads, the front portion 14 with ears 30 may have a width 34 measured in the machine-direction that is about twice that of the width 36 of the center crotch portion 12. The pads are symmetrical about the longitudinal center line axis 32. The ears may have a "height" in the cross-direction defined by cross-directional cut lines I and H. These cross-directional cut lines H and I are shared by the next commonly oriented pad in the repeating pattern. For example, pads X and Z in FIG. 2 are commonly oriented in the repeating pattern and share the cross-directional cut line H. The oppositely oriented or nested pad (pad Y in FIG. 2) is nested against the ears 30 of the respective adjacent pads X and Z. With this particular arrangement, the cut line H defining the ears 30 of adjacent commonly oriented pads X and Z also corresponds to the longitudinal center line 32 of the nested pad Y. This relationship can be particularly seen in FIG. 2.

Still referring to FIG. 2, it can be seen that any individual pad 10 is defined by a series of cut lines. The rearward-most longitudinal point of the back section 15 is defined by-diverging cut lines D and E. Lines D and E meet at the longitudinal center line axis 32 of the pad 10 at a point where a separate cut line A defines ear portions 30 of adjacent and oppositely oriented pads. The crotch section 12 is defined by opposite and parallel cut lines B and C. These lines may be arcuate. The crotch section 12 diverges into the front portion 14 by way of diverging cut lines F and G. An angle of divergence J is defined between the crotch portion and ears of the back portion for any given pad. Because of the nested configuration, this angle J also corresponds to an angle of divergence for an adjacent pad from a forwardmost point of the longitudinal center line axis of a respective pad to its crotch defining line C or B, as particularly seen in FIG. 2. The defining lines F and G between the crotch portion 12 and front portion 14 may be either straight or curved.

An alternate embodiment of a generally T-shaped nested pad configuration is illustrated in FIG. 4. In this particular embodiment, the crotch portion 12 has a first generally constant width (width 36a) section defined by cut lines B' and C'. The back section 15 has a relatively constant width (width 36b) section defined by cut lines B and C. Line B' may be parallel to line B, and line C' may be parallel to line C. In an alternate embodiment, lines B and B' may be curved mirror images of each other. Likewise, lines C and C' may be curved mirror images of each other. The crotch width 36a is less than that of the back section 36b. Diverging lines D' and E' are defined between the crotch section 12 and back section 15. A machine-direction longitudinal centerline 33 of the web strip 24 passes through the midpoints L and K of the defining lines D' and E', respectively. The cut lines D' and E' may be generally straight, as illustrated in the Figure, or may be sinusoidal wherein a zero-node of the sinusoidal line corresponds to the midpoints L and K. The contoured crotch section 12 and back section 15 according to this embodiment may be particularly desired for certain absorbent article applications. By having the center point of the transitional cut lines D' and E' lie along the longitudinal center line axis 33 of the web strip 24, it is ensured that the alternating nested pads 10 have the identical configuration.

It should be appreciated that various contoured profiles of the crotch section 12 may be defined so long as the contours are symmetric with respect to the longitudinal center line axis 32 of the individual pads and, for the oppositely oriented nested pads, are equally distanced from the machine-direction longitudinal center line 33 of the web strip 24.

An alternate embodiment of a cross-directional nested pad configuration 10 is illustrated in FIG. 3. With this embodiment, each individual pad 10 has an overall longitudinal length that is equal to the cross-directional width of the web strip 24. The crotch portion 12 and back portion 15 share common lines. Thus, the crotch portion 12 and back portion 15 of one pad is nested completely between front portions 14 of the immediately adjacent pads. The front portion of a respective pad has a width 34 that is greater than the width 36 of the pad's crotch portion 12 and back portion 15. For example, the width 34 may be twice that of the width 36. The crotch portion 12 and back portion 15 are defined by generally parallel cut lines B and C, and the front portion 14 is defined by the generally parallel cut lines H and I. Lines I and C may be parallel as shown, or may be the curved mirror images of each other. Likewise, lines H and B may be parallel as shown or may be the curved mirror images of each other. Diverging cut lines F and G are defined between the crotch portion 12 and front portion 14. These cut lines F and G may be generally straight, as illustrated in the figure, or may be sinusoidal. The machine-direction longitudinal center line axis 33 of the web 24 passes through the midpoints L and K of the respective cut lines F and G. An angle of divergence J is defined between, for example, cut line B and F, and is equal to the angle of divergence between cut lines F and H. Each pad 10 is symmetric with respect to its longitudinal center line axis 32. With the nested configuration as illustrated in FIG. 3 wherein each individual pad 10 has an overall longitudinal length equal to the cross-directional width of the web strip 24, it can be seen that a single continuous cross-directional cut (lines H, F, and B) is shared by immediately adjacent and oppositely oriented pads such that there is no wastage of the web material between adjacent pads.

Once the web strips 24 have been cut into a cross-directional nested pad configuration according to the invention, the strips may be conveyed directly to an in-line manufacturing process wherein the individual pads 10 are incorporated into a disposable consumer absorbent article, such as diapers, child's training pants, feminine care articles, incontinence articles, swim pants, and the like. Many conventional manufacturing lines for such articles are cross-directional process lines and, thus, the cross-directional orientation of the pads 10 may be easily accommodated into such a processing line. In the event that the absorbent article chassis is not symmetrical, it would be necessary to rotate or flip alternate pads so that all of the pads are oriented longitudinally in the same direction. If the absorbent article chassis is symmetrical, the pads 10 can be accommodated at either orientation. Any manner of automated conventional rotating and positioning modules or units may be used in this regard. Such devices are well known to those skilled in the art.

Alternatively, the web strips 24 having the individual pads 10 defined therein may be formed into a roll or stacked configuration for later incorporation into an in-line manufacturing process. If this is the case, it may be desired not to completely cut each of the individual pads from the web strip. For example, a relatively small percentage of the lines defining the pads may be left uncut so that the web strip 24 maintains its integrity. This would aid in the later feeding of the web strip and individual pads 10 into a manufacturing line. This feature may be accomplished, for example, merely by "interrupting" the blades 28 on the rotary cutter 26 illustrated in FIG. 1. Alternatively, the cut lines may comprise perforated lines wherein the pads are separated into spaced apart individual pads at some later point in the manufacturing process. If the strip 24 maintains its integrity, the strip may be stored, for example, in the form of a roll, or a stacked festooned configuration.

As mentioned, the web strip 24 with individual pads 10 defined therein may be incorporated directly into an in-line absorbent article manufacturing process line. A conceptual schematic representation of this process is provided in FIG. 5. It should be appreciated, however, that FIG. 5 is in no way meant to limit the in-line manufacturing process or machinery utilized in such a process, and is provided merely as conceptually illustrating an example of the invention.

Figure 5:
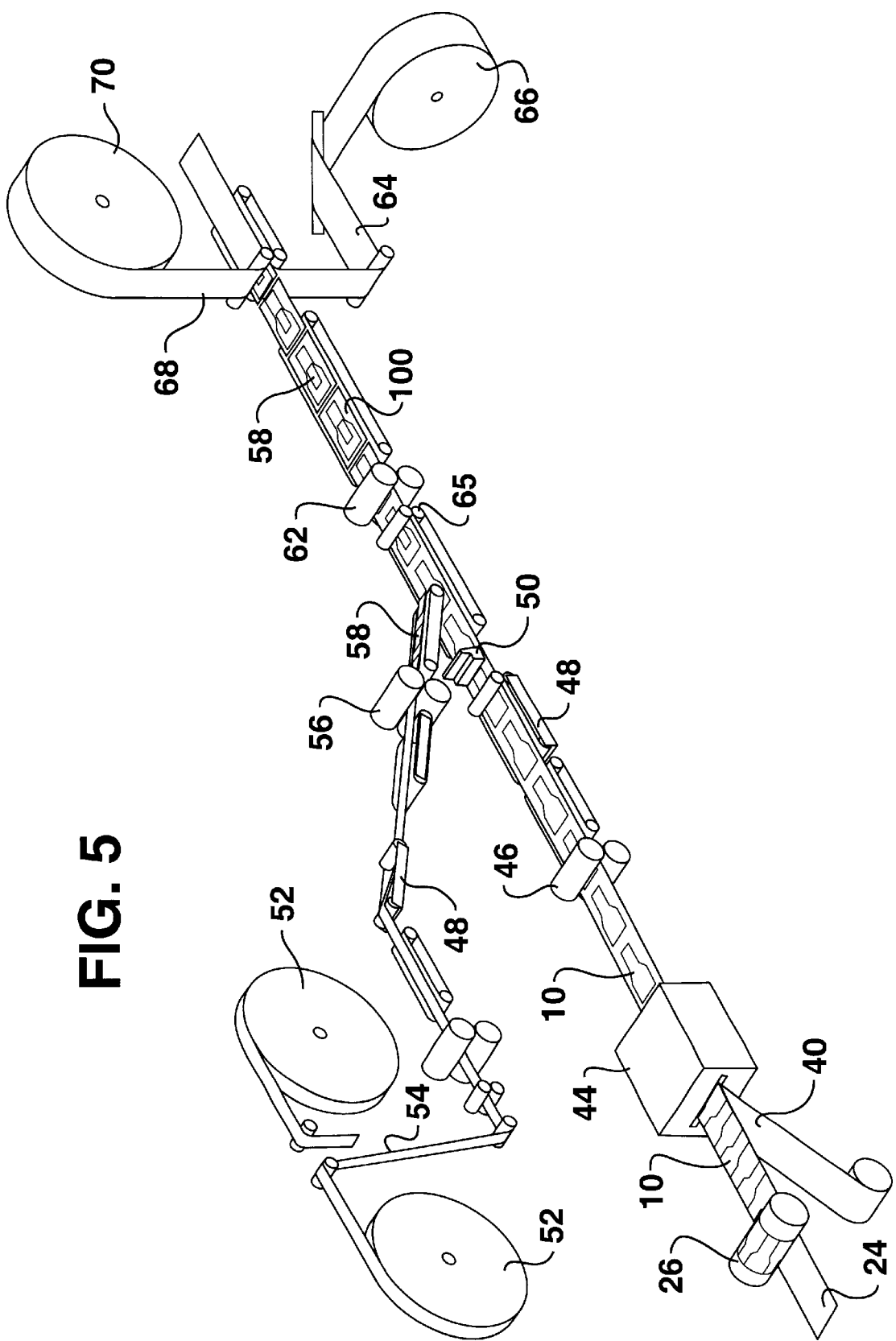
FIG. 5 is a schematic perspective view of an in-line processing method that may incorporate features of the present invention.

Referring to FIG. 5, the strip of absorbent web material 24 is illustrated as being conveyed through a rotary knife cutter 26 so as to define oppositely oriented and cross-directionally nested pads 10, as discussed in detail above. The web strip 24, and other material components of an absorbent article, may be appropriately guided through the manufacturing process with one or more operative guiding mechanisms 48. Various conventional web guide mechanisms 48 can be employed to keep the various webs and materials substantially aligned with respect to a machine-direction center line of the manufacturing process. For example, an absorbent web or a material supplied on a roll can tend to take on a camber if the web is level-wound or processed in any way that bends the web in the cross-machine-direction. Web guides can effectively counteract the effects of this camber. While any operative web guide may be employed, those that minimize the cross-directional bending of the web materials are desired. For example, the web bending can be reduced by minimizing any wrapping of the various webs around an idler roll. Suitable web guides can, for example, include a camber roller FIFE guide, which is available from the FIFE Corporation of Oklahoma City, Okla.

Although not illustrated in FIG. 5, the absorbent web strip 24 may be delivered to a phasing accumulator device, the operation of which is well known in the art. Such an accumulator device can change the running path length of the web strip 24 to selectively advance or retard eventual positioning of the web strip 24 and pads 10 with respect to downstream processing equipment.

Additionally, the manufacturing process may also include compressing of the absorbent web material to reduce its thickness. The compressing may also increase the density of the base web material, and may increase the longitudinal length and/or the cross-directional width of the web. The compressing may be substantially uniformly or non-uniformly applied across the surface of the absorbent web material. The compressing may be configured to emboss a desired pattern of embossments along the machine-direction and/or cross-direction. Referring to FIG. 5, the compressing action can be provided by a counter rotating pair of nip rollers 46. Alternative compressing devices or systems can include converging gap rollers, converging gap conveyor belts or the like, as well as combinations thereof.

An optional first tissue layer 40 may be assembled to the base web strip 24. In one configuration, a bonding device such as provided by an adhesive applicator, may be appropriately disposed to secure the first tissue layer 40 to the underside of the absorbent material strip 24 having the pads 10 defined therein. In the conceptual embodiment of FIG. 5, the web strip 24 with cross-directional nested pads 10 defined therein and first tissue layer 40 are conveyed to a module 44 that rotates the pads 10 to a common longitudinal machine-direction and also spaces the pads 10 apart on the first tissue layer 40 at a desired spacing. Various such modules 44 for rotating and placing items in an in-line manufacturing process are known to those skilled in the art and used in absorbent article manufacturing lines. Certain types of these modules may also perform cutting operations prior to rotating and placing the absorbent pads 10. As an example of such modules 44, reference is made to U.S. Pat. Nos. 6,319,347 B1; 6,139,004; 5,556,504; 5,224,405; 5,104,116; and 4,608,115, the disclosures of which are incorporated herein by reference for all purposes.

At least one supplemental layer of absorbent material may be incorporated with the individual pads 10. In the embodiment illustrated in FIG. 5, this supplemental layer can be provided by pledgets 58. The pledget 58 may be substantially equal to the full length of its associated corresponding absorbent pad 10, or may be shorter than the pad 10. Likewise, the width of each pledget 58 may be equal to, greater than, or less than the smallest width dimension of the corresponding absorbent pad 10. The pledgets 58 may be defined from a suitable pledget web 54 delivered from an operative pledget supply 52 and suitably transported by an operative conveyor. A pledget cutter device 56 may be used to separate the pledget web 51 into a plurality of the individual pledgets 58 to be selectively placed onto the individual absorbent pads 10. The individual pledgets 58 can be positioned at locations that are spaced apart along the machine-direction of the first tissue layer 40 and spaced pads 10. A securing mechanism, such as provided by an adhesive applicator 50 may be used to operatively attach the individual pledgets 58 to the moving tissue 40 and pads 10.

The resulting structure may then be subjected to further conventional downstream processing operations. For example, the assembled components may be processed by a system of assembly nip rollers 65, which can enhance the desired attachments between the assembled components. The resulting structure can then be separated into individual absorbent assemblies 100 by employing a suitable cutter mechanism, such as is represented by the cutter device 62. The assemblies 100 may be further combined with other components, as desired, for example, the absorbent assemblies 100 may be laminated to a layer of liner material 68 provided from a suitable liner supply 70. Additionally, the absorbent assemblies 100 may be combined with a layer of outer cover material 64 provided from a suitable cover supply 66. The composition of such inner and outer liner and cover materials is well known to those skilled in the art, and the invention is not limited to any particular type of material.

It should be understood that the invention encompasses various other embodiments, modifications, and equivalents to the embodiments of the invention described herein which, after reading the description of the invention herein, may suggest themselves to those skilled in the art without departing from the scope and spirit of the present invention.

What is claimed is:

1. A method for making absorbent pads having a longitudinally asymmetric shape between a back portion and front portion thereof, said method comprising:

delivering a supply of an absorbent web material in a machine-direction flow;

cutting the absorbent web material in a cross-direction to form a repeating nested pattern of generally identically shaped and oppositely longitudinally oriented absorbent pads, the pads disposed longitudinally in the cross-direction of the absorbent web; and wherein the absorbent pads are longitudinally asymmetric and nested such that the back portion of one pad is oriented towards the front portions of immediately adjacent pads and adjacent nested pads share defining cut lines such that wastage of the absorbent web material between the nested pads is minimized.

2. The method as in claim 1, wherein there is generally less than about 20% wastage of absorbent material between the nested pads.

3. The method as in claim 1, wherein there is generally zero wastage of absorbent material between the nest pads.

4. The method as in claim 1, wherein the absorbent web material is supplied as a strip from a roll of the web material, the strip having a cross-direction width.

5. The method as in claim 1, wherein the absorbent web material is supplied in the form of a strip having a cross-directional width, the individual absorbent pads having a longitudinal length less than that of the cross-directional width of the web material but a nested pair of the absorbent pads having a combined nested longitudinal length equal to the cross-directional width of the web material.

6. The method as in claim 5, wherein the absorbent pads are symmetrical about a longitudinal centerline axis therethrough.

7. The method as in claim 6, wherein the absorbent pads have a generally T-shaped configuration with a front ear portion having a width measured in the machine-direction of greater than about 1.5 times that of a center crotch portion.

8. The method as in claim 7, wherein an angle of divergence is defined at a cut line between the crotch portion and the ear portion, the cut line also defining an angle of divergence for an adjacent pad from a forward-most point of its longitudinal centerline axis to the crotch portion.

9. The method as in claim 7, wherein cut line between the crotch portion and the ear portion is generally straight.

10. The method as in claim 8, wherein the cut line between the crotch portion and the ear portion is curved.

11. The method as in claim 8, wherein the ear portions have a height defined by a cut line from the longitudinal centerline forward-most point of the adjacent pads to a side of the strip of web material, the ear height cut line being shared by the next commonly oriented pad in the repeating pattern.

12. The method as in claim 6, wherein the absorbent pads have a generally T-shaped configuration with a front ear portion and a crotch portion extending longitudinally at a first width therefrom and diverging to a back portion having a width greater than the width of the crotch portion.

13. The method as in claim 12, wherein the absorbent pads are symmetrical about a longitudinal centerline axis therethrough.

14. The method as in claim 12, wherein a machine-direction centerline axis of the strip of web material passes through a centerpoint of the diverging line between the crotch portion and front portion.

15. The method as in claim 14, wherein the diverging line is generally straight.

16. The method as in claim 14, wherein the diverging line is generally sinusoidal.

17. The method as in claim 12, wherein the crotch portion and back portion have generally parallel sides along their respective width sections.

18. The method as in claim 12, wherein sides of the crotch portion are generally straight and parallel to sides of the back portion of the same pad.

19. The method as in claim 12, wherein sides of the crotch portion are generally curved and the mirror image of sides of the back portion of the same pad.

20. The method as in claim 4, wherein the absorbent pads have a longitudinal length equal to the cross-directional width of the strip of web material.

21. The method as in claim 20, wherein a single cross-directional cut line defines a common side of adjacent nested pads.

22. The method as in claim 20, wherein the absorbent pads are symmetrical about a longitudinal centerline axis thereof.

23. The method as in claim 20, wherein the pads have a front ear portion and a crotch portion extending longitudinally therefrom, wherein an angle of divergence is defined at a cut line between the crotch portion and the ear portion that corresponds to the same angle for the immediately adjacent pad.

24. The method as in claim 23, wherein the cut line between the crotch portion and ear portion is generally straight.

25. The method as in claim 23, wherein the cut line between the crotch portion and ear portion is generally sinusoidal.

26. The method as in claim 23, wherein a machine-direction centerline axis of the strip of web material passes through a center point of the line of divergence between the crotch portions and ear portions of the pads.

27. The method as in claim 20, wherein the crotch and back portions of a pad have parallel cross-directional sides that also define parallel sides of the ear portions for adjacent nested pads.

28. The method as in claim 20, wherein the crotch and back portion of a pad have common sides that are generally parallel to the sides of the ear portions of the same pad.

29. The method as in claim 20, wherein the crotch and back portions of a pad have common curved sides that are generally the mirror image of sides of the ear portions of the same pad.

30. The method as in claim 20, wherein the ear portions have a width measured in the machine-direction that is greater than about 1.5 times that of the crotch portion.

31. A method for making absorbent pads having a longitudinally asymmetric shape between a back portion and front portion thereof, said method comprising:
  delivering a supply of an absorbent web material having generally parallel sides in a machine-direction flow;
  cutting the absorbent web material in a cross-direction dimension of the web material to define a repeating pattern of nested pairs of absorbent pads disposed longitudinally in the cross-direction;
  the cross-direction cuts being made such that a back portion of one pad is oriented towards the front portion of the immediately adjacent pads and each pad shares common cut lines with immediately adjacent pads; and
  wherein the pads are defined with a front portion that is wider in the machine-direction than the crotch portion and the pads are symmetrical along a longitudinal center axis thereof.

32. The method as in claim 31, wherein the crotch portion of one pad is nested completely between the front portions of immediately adjacent pads.

33. The method as in claim 31, wherein the crotch portion of one pad is nested completely between the back portions of immediately adjacent pads.

34. The method as in claim 33, wherein the pads have a longitudinal length equal to a cross-direction width of the web material.

35. The method as in claim 34, wherein adjacent pads share a common cut line disposed at an angle between perpendicular and parallel to the machine-direction sides of the web material such that a longitudinal centerline axis of the web material passes through a center point of the cut line.

36. The method as in claim 35, wherein the angled cut line is straight.

37. The method as in claim 35, wherein the angled cut line is sinusoidal.

38. The method as in claim 31, wherein the front portion of the pads include ears defining a greatest width dimension of the pads, and wherein the ears of alternate pads in the repeating pattern share common cut lines.

39. The method as in claim 38, wherein the crotch portion of the pads is nested between the back portions of the immediately adjacent pads.

* * * * *